United States Patent [19]

Schleyerbach et al.

[11] Patent Number: 5,747,664
[45] Date of Patent: May 5, 1998

[54] N-PHENYL-2-CYANO-3-HYDROXYCROTONAMIDE DERIVATIVES

[75] Inventors: Rudolf Schleyerbach, Hofheim am Taunus; Robert Ryder Bartlett, Darmstadt, both of Germany; Elizabeth Anne Kuo; Edward James Little, both of Swindon, Great Britain

[73] Assignee: Hoechst Aktiengesellschaft, Frankfurt am Main, Germany

[21] Appl. No.: 350,740

[22] Filed: Dec. 7, 1994

Related U.S. Application Data

[63] Continuation of Ser. No. 50,561, Apr. 20, 1993, abandoned, which is a continuation of Ser. No. 963,476, Oct. 21, 1992, abandoned.

[30] Foreign Application Priority Data

Oct. 23, 1991 [DE] Germany .................. 41 34 934.2

[51] Int. Cl.⁶ .................................. C07C 255/17
[52] U.S. Cl. .................................. 558/392; 514/521
[58] Field of Search ..................... 558/392; 514/521

[56] References Cited

U.S. PATENT DOCUMENTS

| | | | |
|---|---|---|---|
| 4,061,767 | 12/1977 | Ertel et al. | 424/282 |
| 4,965,276 | 10/1990 | Bartlett et al. | 514/378 |
| 5,034,410 | 7/1991 | Sjogren et al. | 558/392 X |

FOREIGN PATENT DOCUMENTS

| | | | |
|---|---|---|---|
| 217206-A2 | 4/1987 | European Pat. Off. | |
| 0257882 | 3/1988 | European Pat. Off. | 558/392 |
| 0397052 | 11/1990 | European Pat. Off. | 558/392 |
| 0484223A2 | 5/1992 | European Pat. Off. | 558/392 |
| 2555789 | 7/1977 | Germany | 558/392 |
| 62-103056 | 5/1962 | Japan | 558/392 |

OTHER PUBLICATIONS

R.J. Perper, et al., "The Use of a Standardized Adjuvant Arthritis Assay to Differentiate Between Anti–Inflammatory and Immunosuppressive Agents," Proc. Soc. Exp. Biol. Med. 137 (1971), pp. 506–512.

C.M. Pearson et al., "Studies of Polyarthritis and Other Lesions Induced in Rats by Injection of Mycobacterial Adjuvant. I. General Clinical and Pathologic Characteristics and Some Modifying Factors," Arthrit. Rheum. 2 (1959), pp. 440–459.

*Primary Examiner*—Robert W. Ramsuer
*Attorney, Agent, or Firm*—Finnegan, Henderson, Farabow, Garrett & Dunner, L.L.P.

[57] ABSTRACT

The use of N-phenyl-2-cyano-3-hydroxycrotonamide derivatives of the formula I

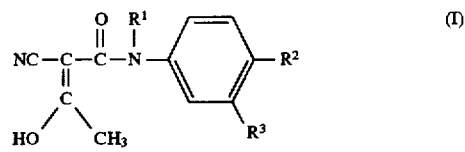

in which $R^1$ is a hydrogen atom or $(C_1-C_4)$-alkyl, $R^2$ is CN, $CX_3$, $WCX_3$, $W(CH_2)_nCX_3$, $NO_2$, $(CH_2)_nCX_3$, or halogen, in which X is halogen, W is an oxygen or sulfur atom and n is an integer from 1 to 3, $R^3$ is $(C_1-C_4)$-alkyl, $(C_3-C_6)$-cycloalkyl, CN or —CO—$R^4$, in which $R^4$ is $(C_1-C_4)$-alkyl or $(C_3-C_6)$-cycloalkyl, and/or their physiologically tolerable salts, for the treatment of rheumatic diseases, auto-immune diseases, and of rejection reactions of the organ recipient to the transplanted organ, is described.

2 Claims, No Drawings

N-PHENYL-2-CYANO-3-HYDROXYCROTONAMIDE DERIVATIVES

This application is a continuation of application Ser. No. 08/050,561, filed Apr. 20, 1993, now abandoned, which is a continuation of application Ser. No. 07/963,476, filed Oct. 21, 1992, abandoned.

U.S. Pat. No. 4,061,767 describes hydroxyethylidenecyanoacetamides which have antiinflammatory and analgesic action.

The use of N-(4-trifluoromethylphenyl)-2-cyano-3-hydroxy crotonamide as a pharmaceutical for the treatment of chronic graft-versus-host diseases and systemic lupus erythematosus has been disclosed EP-A-0,217,206, U.S. Pat. No. 4,965,276.

There is a need for medicaments having antiinflammatory action and for the favorable influencing of immunopathological processes which, by virtue of a more favorable profile of action of the known medicaments, advantageously differ due to better tolerability and more favorable residence time in the body on the one hand and a more causal intervention in the inflammatory process on the other hand. Promising starting points for this are offered by those pharmaceuticals which prevent the excessive formation of the proinflammatory leukotrienes in an increased manner, deactivate highly reactive oxygen free radicals which, as mediators of inflammation, perpetually maintain cell and tissue destruction in the inflammatory rheumatic joints and/ or restore the disturbed immune system.

Surprisingly, N-phenyl-2-cyano-3-hydroxycrotonamide derivatives of the formula I

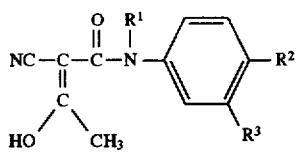
(I)

show pharmacological properties which fulfill the demands made above and are therefore outstandingly suitable for the treatment of, for example, rheumatic diseases or autoimmune diseases or of rejection reactions of the organ recipient to the transplanted organ.

The compounds according to the invention advantageously intervene in the disturbed immune system, as can be demonstrated by suppression of the Arthus reaction and by normalization of the suppressed immune activity in the pathological models of Freund's adjuvant-induced arthritis. In addition, they also show a shorter residence time in the metabolism of the treated organism.

The invention therefore relates to the use of at least one N-phenyl-2-cyano-3-hydroxycrotonamide of the formula I

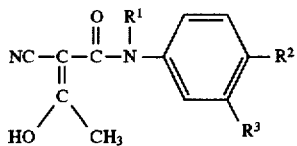
(I)

and/or of at least one of its physiologically tolerable salts, in which $R^1$ is:
 a) a hydrogen atom or
 b) $(C_1-C_4)$-alkyl, which is straight-chain or branched,
$R^2$ is a radical of the group:
 a) $W(CH_2)_nCX_3$,
  W is:
   1) an oxygen atom or
   2) a sulfur atom,
  X is halogen, such as fluorine, chlorine, or iodine,
  n is an integer from 1 to 3,
 b) $WCX_3$,
 c) $CX_3$,
 d) $(CH_2)_nCX_3$,
 e) halogen, such as fluorine, chlorine or iodine,
 f) CN or
 g) $NO_2$,
$R^3$ is a radical of the group:
 a) $(C_1-C_4)$-alkyl, which is straight-chain or branched,
 b) $(C_3-C_6)$-cycloalkyl,
 c) CN or

$R^4$ is:
 1) a hydrogen atom,
 2) $(C_1-C_4)$-alkyl, which is straight-chain or branched, or
 3) $(C_3-C_6)$-cycloalkyl, for the production of pharmaceuticals for the treatment of rheumatic diseases or autoimmune diseases or of rejection reactions of the organ recipient to the transplanted organ.

Preferably, at least one N-phenyl-2-cyano-3-hydroxycrotonamide of the formula I and/or at least one of its physiologically tolerable salts is used, in which $R^1$ is hydrogen,
$R^2$ is a radical of the group:
 a) CN,
 b) halogen, such as fluorine, chlorine or iodine,
 c) $CX_3$,
  X is halogen, such as fluorine, chlorine or iodine, or
 d) $NO_2$,
$R^3$ is a radical of the group:
 a) —$CH_3$,
 b) —CN or

In particular, the following compounds of the formula I and/or their physiologically tolerable salts are used: N-(3-methyl-4-nitrophenyl)-2-cyano-3-hydroxycrotonamide, N-(3-methyl-4-cyanophenyl)-2-cyano-3-hydroxycrotonamide, N-(3-methyl-4-fluorophenyl)-2-cyano-3-hydroxycrotonamide, N-(3-methyl-4-chlorophenyl)-2-cyano-3-hydroxycrotonamide, N-(3-methyl-4-iodinephenyl)-2-cyano-3-hydroxycrotonamide or N-(3-methyl-4-trifluoromethylphenyl)-2-cyano-3-hydroxycrotonamide.

Suitable physiologically tolerable salts of the N-phenyl-2-cyano-3-hydroxycrotonamides of the formula I are, for example, alkali metal, alkaline earth metal or ammonium salts, including those of physiologically tolerable organic ammonium bases.

The invention further relates to novel N-phenyl-2-cyano-3-hydroxycrotonamides of the formula I

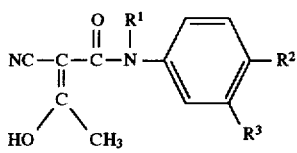

(I)

and/or to at least one of their physiologically tolerable salts, in which $R^1$ is:
a) a hydrogen atom or
b) ($C_1$–$C_4$)-alkyl, which is straight-chain or branched, $R^2$ is a radical of the group:
a) $W(CH_2)_n CX_3$,
   W is:
   1) an oxygen atom or
   2) a sulfur atom,
   X is halogen, such as fluorine, chlorine or iodine,
   n is an integer from 1 to 3,
b) $WCX_3$,
c) $CX_3$,
d) $(CH_2)_n CX_3$,
e) halogen, such as fluorine, chlorine or iodine,
f) CN or
g) $NO_2$, $R^3$ is ($C_3$–$C_6$)-cycloalkyl or

$R^4$ is:
1) a hydrogen atom,
2) ($C_1$–$C_4$)-alkyl, which is straight-chain or branched, or
3) ($C_3$–$C_6$)-cycloalkyl.

Preferred N-phenyl-2-cyano-3-hydroxycrotonamides are those of the formula I and/or at least one of their physiologically tolerable salts, in which $R^1$ is hydrogen, $R^2$ is a radical of the group:
a) CN,
b) halogen, such as fluorine, chlorine or iodine,
c) $CX_3$,
   X is halogen, such as fluorine, chorine or iodine, or
d) $NO_2$, $R^3$ is
a) cyclopropyl or

$R^4$ is cyclopropyl.

The N-phenyl-2-cyano-3-hydroxycrotonamide derivatives of the formula I can be prepared, for example, by the following process:

A compound of the formula II

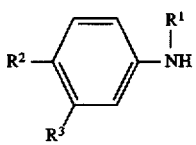

(II)

is reacted with a compound of the formula III

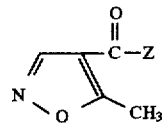

(III)

in which Z is a halogen atom, preferably chlorine or bromine, and $R^1$, $R^2$ and $R^3$ have the meaning given in formula I, and the compound obtained is reacted in the presence of a basic agent to give the corresponding compound of the formula I.

The abovementioned reactions for preparing the compounds of the formula I are carried out under standard conditions in a known manner (U.S. Pat. No. 4,061,767; EP-A-0,217,206).

The compounds of the formula I according to the invention and their corresponding salts are suitable by virtue of their useful pharmacological properties and, at the same time, outstanding tolerability particularly for use as active substances in pharmaceuticals for the treatment of inflammatory rheumatic diseases. They can either be administered on their own, for example in the form of microcapsules, in mixtures with one another or in combination with suitable auxiliaries and/or excipients.

The present invention further relates to the use of at least one N-phenyl-2-cyano-3-hydroxycrotonamide of the formula I and/or at least one of its physiologically tolerable salts for the preparation of pharmaceuticals for the treatment of autoimmune diseases, for example systemic lupus erythematosus, or of chronic graft-versus-host diseases or rejection reactions of the organ recipient to the transplanted organ.

The term organ is understood as meaning all organs in mammals, in particular humans, for example the kidney, heart, skin, liver, pancreas, muscle, bone, intestine or stomach, but also the blood or hair. Rejection reaction means all defence measures of the recipient organism which finally lead to cell or tissue death of the transplanted organ or affect the viability of the transplanted organ. Administration is carried out before, during and after organ transplantation in the recipient and/or donor.

The invention thus also relates to pharmaceuticals which contain at least one N-phenyl-2-cyano-3-hydroxycrotonamide of the formula I and/or at least one of its corresponding acid addition salts or at least one of these active substances in addition to pharmaceutically suitable and physiologically tolerable excipients, diluents and/or auxiliaries.

The pharmaceuticals according to the invention can be administered orally, topically, rectally or, if desired, also parenterally, oral administration being preferred.

Suitable solid or liquid pharmaceutical preparation forms are, for example, granules, powders, coated tablets, tablets, (micro)capsules, suppositories, syrups, juices, suspensions, emulsions, drops or injectable solutions as well as preparations with protracted release of active substance, in whose preparation auxiliaries, such as excipients, disintegrants, binders, coating agents, swelling agents, lubricants, flavorings, sweeteners or solubilizers are customarily used. Commonly used auxiliaries which may be mentioned are, for example, magnesium carbonate, titanium dioxide, lactose, mannitol and other sugars, talc, lactalbumin, gelatin, starch, cellulose and its derivatives, animal and vegetable oils, polyethylene glycols and solvents, such as, for example, sterile water and mono- or polyhydric alcohols, for example glycerol.

The pharmaceutical preparations are preferably prepared and administered in dose units, each unit containing a certain dose of at least one compound according to formula I and/or at least one corresponding acid addition salt as the active constituent. In solid dose units, such as tablets, capsules, coated tablets or suppositories, this dose can be up to about 300 mg, but preferably about 100 to 200 mg.

For the treatment of an adult patient suffering from inflammatory rheumatic diseases—depending on the activity of the compounds according to formula I and/or the corresponding salts in humans—daily doses of about 5 to 300 mg of active substance, preferably about 25 to 100 mg, are indicated on oral administration. Under certain circumstances, however, higher or lower daily doses may also be appropriate. The administration of the daily dose can be carried out both by single administration in the form of an individual dose unit or else several smaller dose units and by multiple administration of subdivided doses at specific intervals.

Finally, the compounds of the formula I and the corresponding acid addition salts can also be formulated together with other suitable active substances, for example antiuricopathics, thrombocyte aggregation inhibitors, analgesics and other steroidal or non-steroidal antiinflammatories, during the production of the abovementioned pharmaceutical preparation forms.

The structure of the compounds described below was confirmed by elemental analysis, IR and $^1$H-NMR spectra.

EXAMPLE 1
N-(3-Methyl-4-nitrophenyl)-2-cyano-3-hydroxycrotonamide

Cyanoacetic acid (1.5 g; 17.6 mmol) and phosphorus pentachloride (4.1 g; 19.4 mmol) are heated under reflux in dichloromethane (40 ml) for 1 hour. 3-Methyl-4-nitroaniline (1.6 g; 10.6 mmol) is added and the mixture is heated for a further hour under reflux conditions. After cooling, the solid is filtered and stirred with water for a further hour, the mixture is filtered and the filtrate is brought to dryness under reduced pressure. 2-Cyano-N-(3-methyl-4-nitrophenyl) acetamide (1.4 g; 64%) is thus obtained.

2-Cyano-N-(3-methyl-4-nitrophenyl)acetamide (0.61 g; 2.8 mmol) is dissolved in tetrahydrofuran (30 ml) and sodium hydride (80% strength dispersion in oil; 0.21 g; 7 mmol) is added. The mixture is stirred at 25° C. for 15 minutes and 1-acetylimidazole (0.46 g; 4.2 mmol) is added dropwise over the course of 5 minutes and the mixture is stirred for a further 15 minutes. 2 ml of glacial acetic acid are added and the mixture is stirred at 25° C. for 1 hour and then poured into ice-cold water (100 ml). The pH of the solution is then adjusted to 1 using concentrated hydrochloric acid, and the precipitate is filtered, washed with water and brought to dryness under reduced pressure. N-(3-Methyl-4-nitrophenyl)-2-cyano-3-hydroxycrotonamide is thus obtained.

Yeild: 0.65 g (88% of theory)

Melting point: 231° to 233° C.

$C_{12}H_{11}N_3O_4$ (molecular weight (MW)=261.24)

The following compounds of the formula I are prepared analogously to the above example.

EXAMPLE 2
N-(3-Methyl-4-cyanophenyl)-2-cyano-3-hydroxycrotonamide

Melting point: 239° to 240° C.

$C_{13}H_{11}N_3O_2$(MW=241.25)

EXAMPLE 3
N-(3-Methyl-4-fluorophenyl)-2-cyano-3-hydroxycrotonamide

Melting point: 167.5° to 168° C.

$C_{12}H_{11}FN_2O_2$(MW=234.23)

EXAMPLE 4
N-(3-Methyl-4-chlorophenyl)-2-cyano-3-hydroxycrotonamide

Melting point: 184° C.

$C_{12}H_{11}ClN_2O_2$ (MW=250.69)

EXAMPLE 5
N-(3-Methyl-4-iodinephenyl)-2-cyano-3-hydroxycrotonamide

Melting point: 177° to 178° C.

$C_{12}H_{11}JN_2O_2$ (MW=342.14)

EXAMPLE 6
N-(3-methyl-4-trifluoromethylphenyl)-2-cyano-3-Hydroxycrotonamide

Melting point: 182° to 184° C.

$C_{13}H_{11}F_3N_2O_2$ (MW=284.23)

Pharmacological Testing and Results

The testing of the compounds of the formula I according to the invention for antiinflammatory action and for the effect on immunopathological processes is carried out in the animal models described below.

Animal Model 1.

Carrageenan paw edema

The investigations are carried out by the method of Winter et al. (J. Pharmacol. Exp. Ther. 141, 369 (1963).

The experimental animals used are male rats of a CFHB strain having a body weight between 160 and 180 g which have fasted for about 17 hours. By subplantar injection (left paw) of 0.2 ml of 0.5% strength carrageenan suspension in 0.9% NaCl per animal, an edema is formed in the locality of the injection site whose extent is determined plethysmographically. 1 hour before administration of carrageenan, the test substances are administered orally by stomach tube in carboxymethylcellulose (CMC suspensions) at an injection volume of 1 ml/100 g of body weight, and 3 hours after this administration the paw volume is determined. A color marking on the tarsocrural joint is used to standardize the depth of immersion. Number of experimental animals: n=6–12 per dose.

Animal Model 2.

Delayed hypersensitivity in mouse paw edema

Mice (8 to 10, male CD-1, weight 25 to 30 g) are sensitized by a subcutaneous injection of 1 mg of methylbovineserumalbumin (MBSA) in 0.2 ml of a physiological Freund's complete adjuvant (FCA) emulsion. A control group receives injections of physiological FCA. 7 days after sensitization, 0.1 mg of MBSA in 0.05 ml of a physiological saline solution is injected into the right rear paw. The paw edemas are determined 24 hours later. Injections of physiological saline solution in the left paw are used as control. The compounds according to the invention are administered orally. Administrations are carried out on the 4th, 5th, 6th and twice on the 7th day, one hour before and 6 hours after the further MBSA injection.

Animal Model 3.

Delayed hypersensitivity in rat paw edema

Rats (8 to 12, male CFHB, weight 160 to 180 g) are sensitized by injection in the tail as in Test 2. In contrast to Test 2, 0.4 mg of Mycobacterium tuberculosis antigen in 0.2 ml of physiological saline solution are administered on the 7th day, otherwise the experimental conditions are as in Test 2.

The paw volume compared with the control group is used as the assessment criterion for the abovementioned animal models. The inhibition of the increase in paw volume is given in percentage values.

Table 1 shows the results; the dose of the compounds according to the invention in mg/kg is given in brackets.

TABLE 1

| Example No. | Animal model 1 | Animal model 2 | Animal model 3 |
|---|---|---|---|
| 1 | 1 (50) | 53 (100) | 90 (50) |
| 2 | −20 (50) | 41 (100) | 88 (50) |
| 3 | −1 (50) | 52 (100) | 70 (50) |
| 4 | 12 (50) | 78 (100) | 45 (50) |
| 5 | 7 (50) | n.d. | 28 (50) |
| 6 | 37 (50) | n.d. | n.d. | n.d. = not determined

4. Adjuvant-Induced Polyarthritis

The investigations are carried out by the methods of Pearson and Perper [Pearson, C. M. and F. D. Wood, Arth. Rheum. 2,44 (1959); Perper, R. J. et al., Proc. Soc. Exp. Biol. Med. 137, 506 (1971)]. The experimental animals used are male Wistar-Lewis rats (Mollegaard, Denmark) having a body weight between 160 and 200 g. Polyarthritis is induced by injection of 0.1 ml of Freund's adjuvant (corresponds to about 6 mg of Mycobacterium butyricum suspension, Difco Labs./Detroit, per ml in liquid paraffin, Merck/Darmstadt) in the left rear paw. The injection results in immunopathoogical processes which lead to chronic inflammations within 10 to 14 days. It leads in particular to poly- and periarthritic symptoms in other body parts and also in the right rear paw.

The test substances are administered orally in CMC-suspension. The injection volume is 1 mg/100 g of body weight of the rats. The administration of the compounds according to the invention is carried out on 12 successive days, starting with the adjuvant injection. 21 days after injection, the paw volume of both rear paws is measured. CMC suspensions are used as control.

The paw volume compared with the control group is used as the evaluation criterion. The inhibition of the increase in paw volume is given in percentage values. Table 2 shows the results; the dose of the compounds according to the invention in mg/kg is given in brackets.

TABLE 2

| | Inhibition of the increase in paw volume | |
|---|---|---|
| Example No. | Left paw (injected) | right paw (not injected) |
| 1 | 65 (25) | 87 (25) |
| 2 | 0 (25) | 31 (25) |
| 3 | 14 (25) | 0 (25) |

TABLE 2-continued

| | Inhibition of the increase in paw volume | |
|---|---|---|
| Example No. | Left paw (injected) | right paw (not injected) |
| 4 | 15 (25) | 0 (25) |
| 5 | 26 (25) | 34 (25) |
| 6 | 74 (25) | 87 (25) |

Degradation Time in Vivo

The test substances are administered orally in CMC suspension. The volume is 1 mg/100 g of body weight of the rats and 3 mg/100 g of body weight of the mice. The comparison substance used is N-(4-trifluoromethylphenyl)-2-cyano-3-hydroxycrotonamide. The determination of the concentrations of the comparison substance and the test substances in the serum was carried out after oral administration of the substances.

Table 3 shows the results.

TABLE 3

| Test substance Example No. | Concentration (µg/ml) | | | | | |
|---|---|---|---|---|---|---|
| Time (hours) | 1 | 3 | 6 | 24 | 48 | 72 |
| 4 Mouse | 67.7 | 59.3 | 45.4 | 0 | 0 | 0 |
| Rat | 2.4 | 1.4 | 0.2 | 0 | 0 | 0 |
| 6 Mouse | 64.5 | 85.0 | 76.7 | 0.44 | 0.1 | 0.1 |
| Rat | 11.6 | 22.6 | 25.4 | 0 | 0 | 0 |
| Comparison substance | | | | | | |
| Mouse | 114.4 | 126.7 | 125.9 | 113.2 | 62.6 | 36.7 |
| Rat | 20.3 | 42.8 | 43.4 | 5.8 | 1.3 | 0.2 |

We claim:

1. An N-phenyl-2-cyano-3-hydroxycrotonamide of the formula I

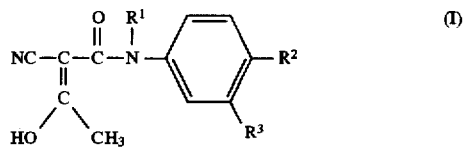

or its physiologically tolerable salts, in which $R^1$ is:
  a) a hydrogen atom or
  b) ($C_1$–$C_4$)-alkyl, which is straight-chain or branched, $R^2$ is a radical of the group:
  a) $W(CH_2)_nCX_3$,
    W is:
      1) an oxygen atom or
      2) a sulfur atom,
    X is fluorine, chlorine, or iodine,
    n is an integer from 1 to 3,
  b) $WCX_3$,
    W is:
      1) an oxygen atom or
      2) a sulfur atom,
    X is fluorine, chlorine, or iodine,
  c) $CX_3$, X is fluorine, chlorine, or iodine,
  d) $(CH_2)_nCX_3$, X is fluorine, chlorine, or iodine, n is an integer from 1–3, e) fluorine, chlorine, or iodine,
f) CN or
g) $NO_2$.

$R^3$ is $(C_3-C_6)$-cycloalkyl or

$R^4$ is:
1) a hydrogen atom,
2) $(C_1-C_4)$-alkyl, which is straight-chain or branched or,
3) $(C_3-C_6)$-cycloalkyl.

2. An N-phenyl-2-cyano-3-hydroxycrotonamide of the formula I as claimed in claim 1 or its physiologically tolerable salts, in which $R^1$ is hydrogen, $R^2$ is a radical of the group:
a) CN,
b) fluorine, chlorine or iodine,
c) $CX_3$,
   X is fluorine, chlorine or iodine, or
d) $NO_2$.

$R^3$ is
a) cyclopropyl or

$R^4$ is cyclopropyl.

* * * * *